United States Patent
Vanney et al.

[11] Patent Number: 5,876,436
[45] Date of Patent: Mar. 2, 1999

[54] ROTATABLE CUFF ASSEMBLY FOR A HEART VALVE PROSTHESIS

[75] Inventors: Guy P. Vanney, Blaine; Michael J. Girard, Lino Lakes; William R. Kramlinger, Shoreview; Jonas A. Runquist, Minneapolis; Kimberly A. Anderson, Eagan; Scott D. Moore, Columbia Heights; Bob Allan, Maple Grove, all of Minn.; James E. Graf, Littleton, Colo.

[73] Assignee: St. Jude Medical, Inc., St. Paul, Minn.

[21] Appl. No.: 799,289

[22] Filed: Feb. 13, 1997

(Under 37 CFR 1.47)

Related U.S. Application Data

[63] Continuation of Ser. No. 327,164, Oct. 21, 1994, abandoned.

[51] Int. Cl.⁶ .................................................. A61F 2/24
[52] U.S. Cl. .................................. 623/2; 623/900
[58] Field of Search ............................... 623/2, 66, 900, 623/901; 137/515.7

[56] References Cited

U.S. PATENT DOCUMENTS

| | | | |
|---|---|---|---|
| Re. 30,507 | 2/1981 | Kaster | 3/1.5 |
| 3,099,016 | 7/1963 | Edwards | 3/1 |
| 3,143,742 | 8/1964 | Cromie | 3/1 |
| 3,409,013 | 11/1968 | Berry | 128/303 |
| 3,491,376 | 1/1970 | Shiley | 3/1 |
| 3,579,642 | 5/1971 | Heffernan et al. | 3/1 |
| 3,628,535 | 12/1971 | Ostrowsky et al. | 128/303 |
| 3,691,567 | 9/1972 | Cromie | 3/1 |
| 3,725,961 | 4/1973 | Magovern et al. | 3/1 |
| 3,727,240 | 4/1973 | Child | 3/1 |
| 3,763,548 | 10/1973 | Anderson | 29/445 |
| 3,781,969 | 1/1974 | Anderson | 29/445 |
| 3,800,403 | 4/1974 | Anderson et al. | 29/445 |
| 3,825,957 | 7/1974 | Kaster | 3/1 |
| 3,828,787 | 8/1974 | Anderson et al. | 128/303 |
| 3,839,741 | 10/1974 | Haller | 3/1 |
| 3,859,668 | 1/1975 | Anderson | 3/1 |
| 3,959,827 | 6/1976 | Kaster . | |
| 3,996,623 | 12/1976 | Kaster | 3/1.5 |
| 3,997,923 | 12/1976 | Possis | 3/1.5 |
| 4,078,268 | 3/1978 | Possis | 3/1.5 |
| 4,197,593 | 4/1980 | Kaster et al. | 3/1 |
| 4,233,690 | 11/1980 | Akins | 3/1.5 |
| 4,240,161 | 12/1980 | Huffstutler, Jr. et al. | 3/1.5 |
| 4,276,658 | 7/1981 | Hanson et al. . | |
| 4,328,592 | 5/1982 | Klawitter | 3/1.5 |
| 4,535,483 | 8/1985 | Klawitter et al. | 623/2 |
| 4,576,605 | 3/1986 | Kaidash et al. | 623/2 |
| 4,599,081 | 7/1986 | Cohen | 623/2 |
| 4,655,462 | 4/1987 | Balsells | 277/164 |
| 4,665,906 | 5/1987 | Jervis | 128/92 |
| 4,666,442 | 5/1987 | Arru et al. | 623/2 |
| 4,680,031 | 7/1987 | Alonso | 623/2 |
| 4,683,883 | 8/1987 | Martin | 128/303 R |
| 4,705,516 | 11/1987 | Barone et al. | 623/2 |
| 4,743,253 | 5/1988 | Magladry | 623/2 |
| 4,790,843 | 12/1988 | Carpentier et al. | 623/2 |
| 4,826,144 | 5/1989 | Balsells | 267/167 |
| 4,863,460 | 9/1989 | Magladry | 623/2 |
| 4,865,600 | 9/1989 | Carpentier et al. | 623/2 |
| 4,876,781 | 10/1989 | Balsells | 29/173 |
| 4,890,944 | 1/1990 | Cousins et al. | 401/98 |
| 4,915,366 | 4/1990 | Balsells | 267/167 |
| 4,982,727 | 1/1991 | Sato | 128/4 |

(List continued on next page.)

*Primary Examiner*—Mickey Yu
*Assistant Examiner*—Francis K. Cuddihy
*Attorney, Agent, or Firm*—Hallie A. Finucane, Esq.; Westman, Champlin & Kelly, P.A.

[57] ABSTRACT

The invention provides a sewing cuff assembly for mounting to the body of a heart valve prosthesis. The sewing cuff assembly comprises a resiliently deformed spring for exerting a force directed toward the orifice structure. When a torque is applied to the valve, the force results in a rotation-resisting torque sufficient to resist rotation during normal operation of the valve after implantation but low enough to permit assisted rotation, as during surgery.

21 Claims, 3 Drawing Sheets

U.S. PATENT DOCUMENTS

| | | | |
|---|---|---|---|
| 5,035,709 | 7/1991 | Wieting et al. | 623/2 |
| 5,071,431 | 12/1991 | Sauter et al. | 623/2 |
| 5,072,070 | 12/1991 | Balsells | 174/35 |
| 5,079,388 | 1/1992 | Balsells | 174/35 |
| 5,104,406 | 4/1992 | Curcio et al. | 623/2 |
| 5,108,078 | 4/1992 | Balsells | 267/167 |
| 5,117,066 | 5/1992 | Balsells | 174/35 |
| 5,163,955 | 11/1992 | Love et al. | 623/2 |
| 5,178,633 | 1/1993 | Peters | 623/2 |
| 5,197,980 | 3/1993 | Gorshkov et al. | 623/2 |
| 5,236,450 | 8/1993 | Scott | 623/2 |
| 5,354,330 | 10/1994 | Hanson et al. | 623/2 |
| 5,403,305 | 4/1995 | Sauter et al. | 606/1 |
| 5,443,502 | 8/1995 | Caudillo et al. | 623/2 |
| 5,480,425 | 1/1996 | Ogilive | 623/2 |
| 5,582,607 | 12/1996 | Lackman | 606/1 |
| 5,584,879 | 12/1996 | Reimold et al. | 623/2 |
| 5,607,470 | 3/1997 | Milo | 623/2 |

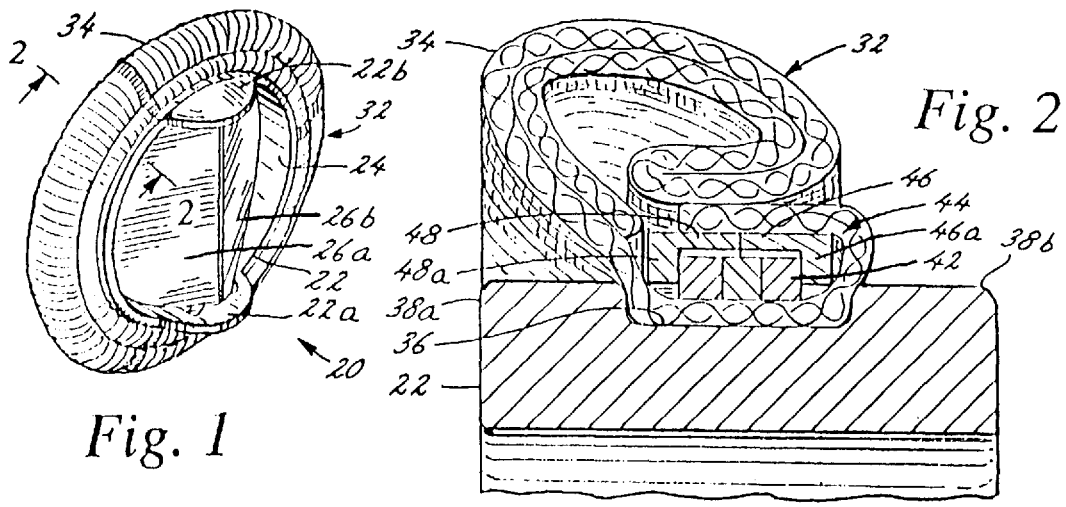
Fig. 1
Fig. 2
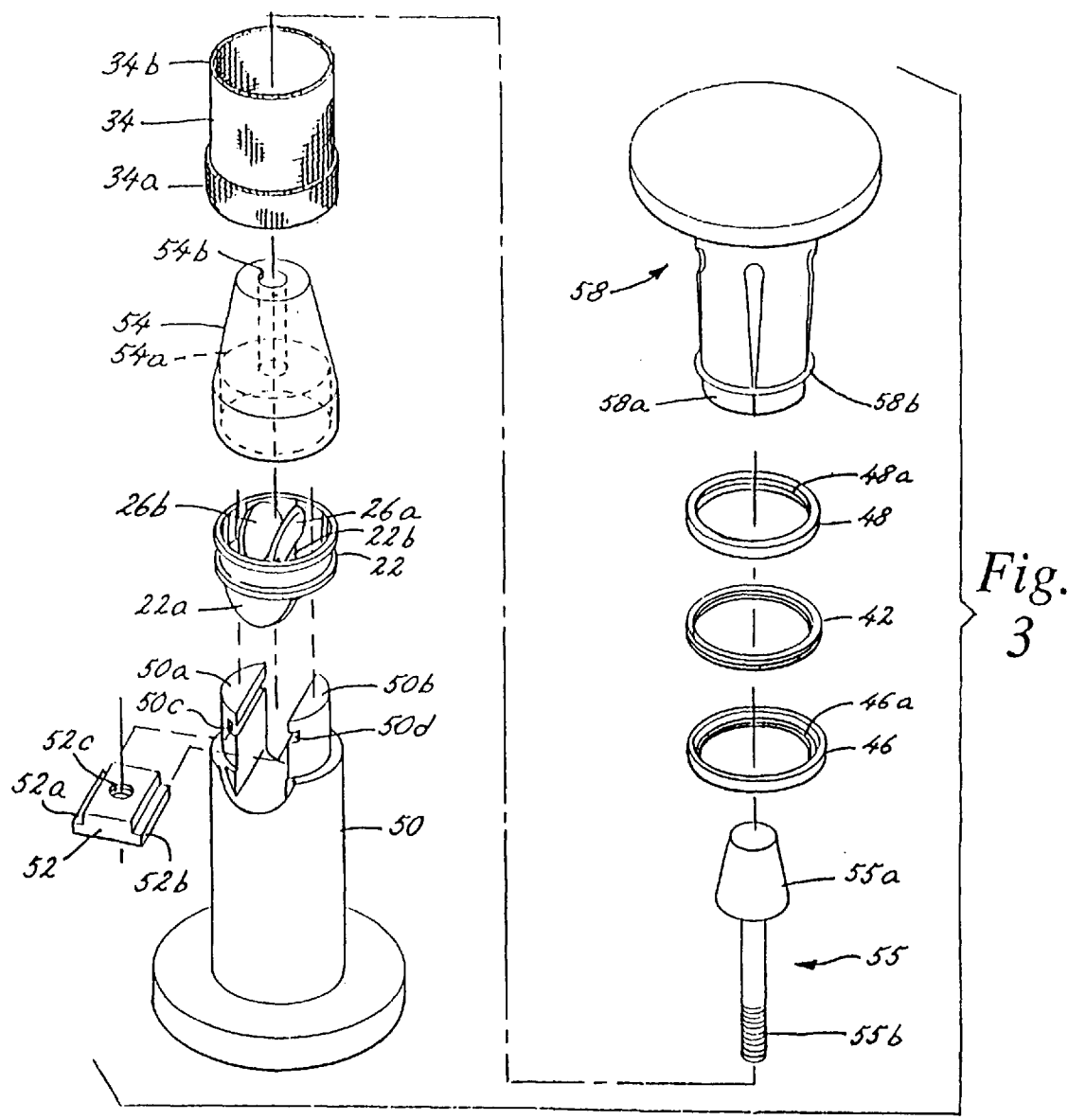
Fig. 3

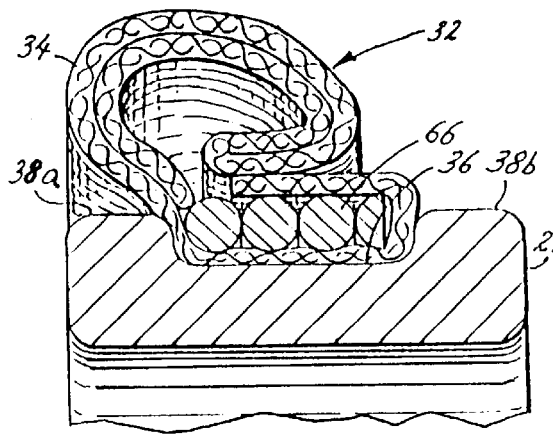
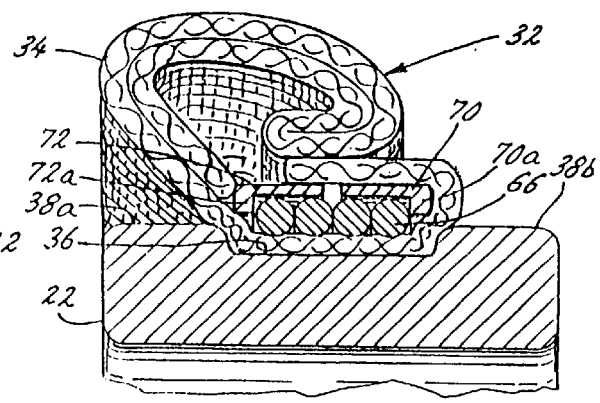
Fig. 4        Fig. 5
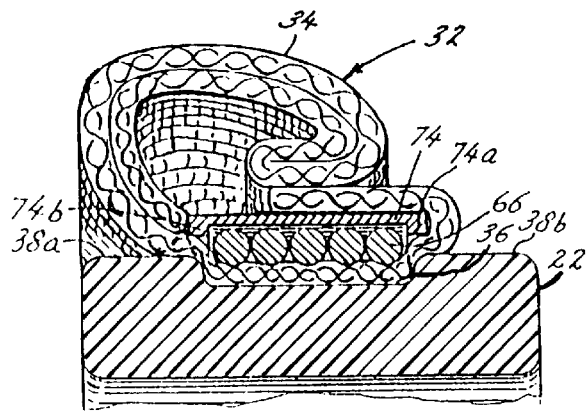
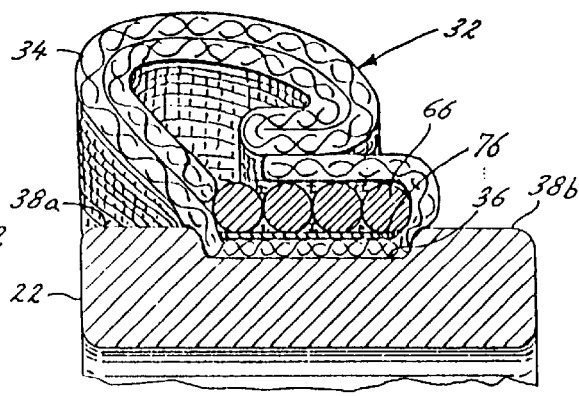
Fig. 6        Fig. 7
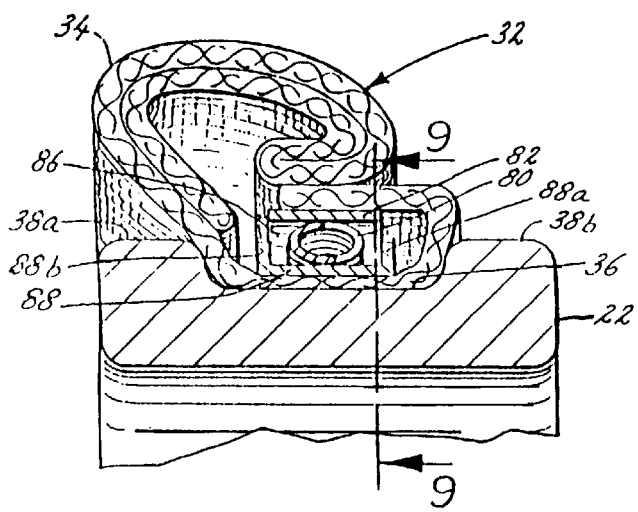
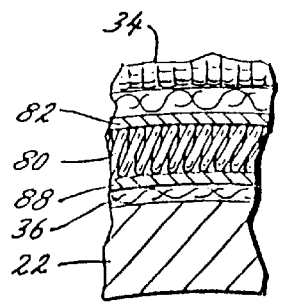
Fig. 8        Fig. 9

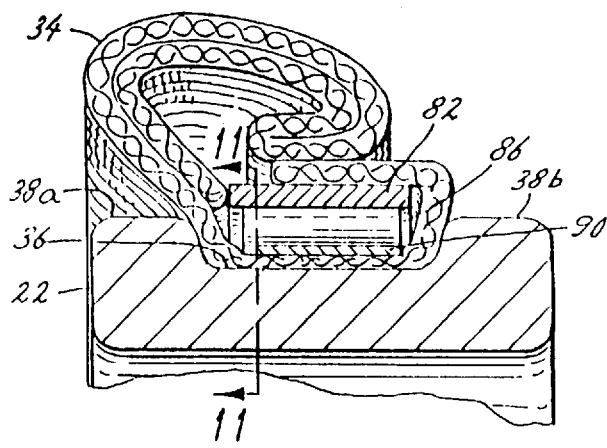
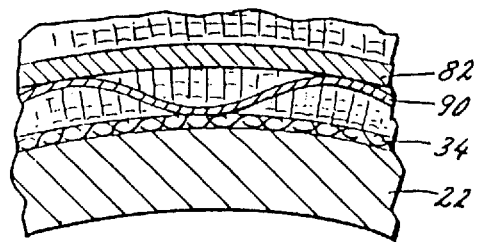
Fig. 10          Fig. 11
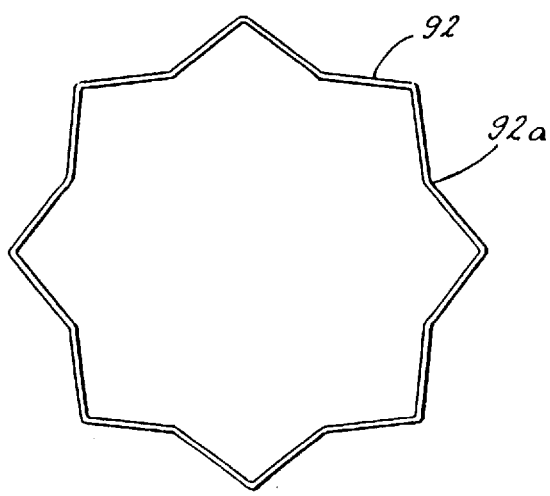
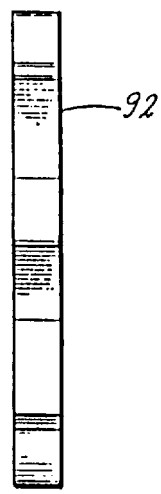
Fig. 12          Fig. 13
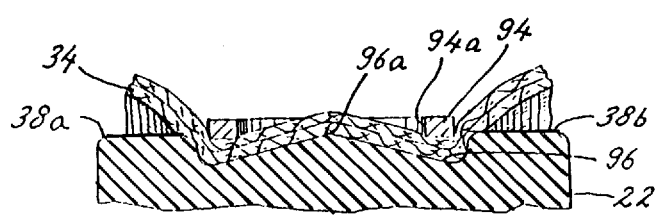
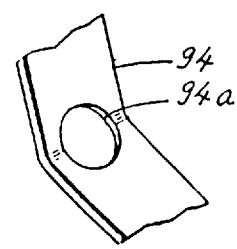
Fig. 14          Fig. 15

ROTATABLE CUFF ASSEMBLY FOR A HEART VALVE PROSTHESIS

This is a File Wrapper Continuation of application Ser. No. 08/327,164, filed Oct. 21, 1994, now abandoned.

FIELD OF THE INVENTION

The invention relates generally to heart valve prostheses, and more specifically to sewing cuff assemblies for implanting heart valves.

BACKGROUND OF THE INVENTION

Artificial heart valves, which may be implanted in the human heart to replace natural valves, are essentially check valves which permit the flow of blood through the valves in a downstream direction, but block regurgitation of blood in a reverse or upstream direction. Heart valve prostheses typically fall into one of two categories—mechanical valves and tissue valves. The present invention finds its principal application in the field of mechanical valves, although it is not limited to this application as it may be used, for example, for tissue valves. Such mechanical valves generally include an annular valve housing or body having a central orifice which provides a passageway for blood. A valving mechanism, typically including occluders, is mounted in the orifice and opens and closes to regulate the passage of blood. One such valve which has enjoyed considerable success is disclosed in commonly assigned U.S. Pat. No. 4,276,658.

The outer circumferential surface of the valve body disclosed in the '658 patent includes a groove, which has facilitated the coupling of a suturing ring or sewing cuff to the valve body. The sewing cuffs for heart valve prostheses are generally a soft, flexible torus-like element through which sutures may pass to secure the sewing cuff, and consequently the heart valve, to the heart tissue.

Another method of coupling the sewing cuff to the valve body is shown in U.S. Pat. No. 5,071,431 to Sauter et al. Sauter et al. discloses a heart valve where a sewing cuff which is attached to a stiffening ring, with the stiffening ring being coupled to the valve body by a locking ring which rides in grooves in the outer periphery of the valve body and the inner periphery of the stiffening ring.

After a damaged or diseased natural valve structure is removed from the patient, the prosthesis is typically seated in the proper orientation and the sewing cuff is sewn to the peripheral heart tissue. Depending on the particular valve structure, care must be taken to ultimately orient the valve occluders to ensure that the valving mechanism is in the most favorable anatomical position to provide proper blood flow and to ensure that the valve operates without interference from surrounding heart tissue. This must either be done as the sewing cuff of the valve is sutured into place, or if the sewing cuff is rotatable relative to the valve, this can be done after the sewing cuff is secured to the heart tissue. While this latter arrangement is convenient and can obviate the need to remove and resuture a valve to effect a rotation, a rotatable valve must meet several criteria.

For example, the torsional force required to rotate the valve must be low enough so that the surgeon is able to rotationally position the valve with ease and without damage to the surrounding tissue. Once implanted, however, the valve body must maintain the desired position during the remainder of the surgery, and thereafter. Consequently, the torque required to initiate rotation must be great enough to prevent spontaneous in vivo rotation. Thus, the torsional force required to rotate the valve body within the sewing cuff should be predictable and fall within a narrow predetermined range such that it may be easily adjusted by the surgeon, yet be resistant to undesirable in vivo rotation once implanted. Moreover, the desired torque characteristics should be repeatable from valve to valve without significant variation.

The torsional force required to rotate the valve body relative to the sewing cuff will be determined by the manner in which the sewing cuff is retained on the valve body. Various methods have been proposed to rotatably secure the sewing cuffs of heart valve prostheses to the valve bodies. For example, U.S. Pat. No. 4,197,593 to Kaster et al. discloses a heart valve where a sewing cuff is sutured to a polymeric slip ring that slides along the surface of the valve body. U.S. Pat. No. 4,535,483 to Klawitter et al. discloses a heart valve where the sewing cuff is carried by deformable metal retainer rings which engage a stiffening ring disposed in and secured to a peripheral groove in the valve body. U.S. Pat. No. 5,104,406 to Curicio et al. discloses a heart valve where the fabric of the sewing cuff is stitched to a core, which directly abuts and rides the groove in the valve body; the core and the valve additionally sandwich the fabric along the annular space where the fabric is stitched to the core. U.S. Pat. No. 5,178,633 to Peters discloses a heart valve where the sewing cuff is coupled to the valve body by continuous fastener bands. The frictional engagement between the fabric tube and the valve body or "orifice ring" is controlled by the internal diameter of the fastener bands, which may be manufactured with precision. A need exists for an improved rotatable heart valve prosthesis.

BRIEF SUMMARY OF THE INVENTION

The invention provides a heart valve prosthesis in which the sewing cuff is rotatably mounted to the valve body by a resiliently deformed spring which is disposed along a circumferential surface or annular seat of the valve body. The spring exerts a controlled force on the valve body, which results in a rotation-resisting torque when an outside force is applied to the valve. The rotation-resisting torque is sufficient to resist rotation during normal operation of the valve after implantation but low enough to permit the surgeon to rotate the valve during implantation.

Preferably, the valve body includes annular shoulders along either side of the annular seat. Once assembled between the shoulders, the spring is held in axial alignment with the annular seat by the shoulders.

The deformation of the spring may be provided as a result of the structural relationship between the spring itself and the annular seat, as when the spring is smaller than the annular seat in an unstressed state, and is expanded to fit about the valve body. Helical springs having square, round or rectangular cross-sections are particularly suited for this design in that the coils of the helix may readily be formed to a smaller diameter yet can be manually expanded for coiling around the valve body. Once in place, the spring exerts a radially-inward force on the annular valve seat.

The inventive valve design also preferably includes a restraining ring element which is disposed circumferentially about the spring. The restraining ring element restrains outward expansion of the spring, and, therefore, minimizes gaps between the fabric of the sewing cuff and the valve body when, for example, a concentrated separation force is applied to the sewing cuff during preparation and/or implantation. Thus, the restraining ring element provides excellent cuff retention and increases the overall integrity of the heart valve.

In addition to preventing separation of the sewing cuff from the valve, the restraining ring can also be used to assist in the resilient deformation of the spring. When used in this manner, the spring may be deformed as a result of the relationship between the ring element, the annular seat, and the spring. More specifically, the spring may be deformed in an annulus defined between the annular seat and the ring element. With such a design, the spring exerts a radially-outward force, which the ring element restrains, and a radially-inward force applied to the annular seat, which results in the rotation-resisting torque when a rotating force is applied to the valve. Thus, the ring element continuously restrains an outward force exerted by the spring, rather than only restraining the spring when an external separation force is applied. Long, relatively small diameter helical springs and undulating springs are particularly suitable in this application.

These and other features and advantages of the invention will be more readily apparent upon reading the following description of a preferred exemplified embodiment of the invention and upon reference to the accompanying drawings in which:

BRIEF DESCRIPTION OF THE DRAWINGS

FIG. 1 is a perspective view of the invention;

FIG. 2 is a sectional view of the preferred embodiment of the invention taken along line 2—2 in FIG. 1;

FIG. 3 is an exploded perspective view of the preferred embodiment of the invention and an assembly fixture for assembling the invention;

FIG. 4 is a sectional view similar to that of FIG. 2 showing a first alternate embodiment of the invention;

FIG. 5 is a sectional view similar to that of FIG. 2 showing a second alternate embodiment of the invention;

FIG. 6 is a sectional view similar to that of FIG. 2 showing a third alternate embodiment of the invention;

FIG. 7 is a sectional view similar to that of FIG. 2 showing a fourth alternate embodiment of the invention;

FIG. 8 is a sectional view similar to that of FIG. 2 showing a fifth alternate embodiment of the invention;

FIG. 9 is a sectional view taken along line 9—9 in FIG. 8;

FIG. 10 is a sectional view similar to that of FIG. 2 showing a sixth alternate embodiment of the invention;

FIG. 11 is a sectional view taken along line 11—11 in FIG. 10;

FIG. 12 is a plan view of a spring element utilized in a seventh embodiment of the invention;

FIG. 13 is a side view of the spring element shown in FIG. 12;

FIG. 14 is a fragmentary sectional view of an eighth embodiment of the invention; and FIG. 15 is fragmentary view of the spring element shown in FIG. 14, which is similar to that shown in FIGS. 12 and 13.

While the invention will be described in connection with certain preferred embodiments, there is no intent to limit it to those embodiments. On the contrary, the intent is to cover all alternatives, modifications, and equivalents included within the spirit and scope of the invention as defined by the appended claims.

DETAILED DESCRIPTION OF THE INVENTION

Turning now to the drawings, there is shown in FIG. 1 a heart valve prosthesis 20 constructed in accordance with the invention. The heart valve 20 shown in FIG. 1 is an aortic valve. It will appreciated, however, that the invention applies equally to other valve prostheses, including mitral valves. The exemplary heart valve 20 shown is essentially the same as that disclosed in U.S. Pat. No. 4,276,658, incorporated herein by reference. The valve 20 includes an annular valve housing or body 22 having an annular orifice 24 therethrough and leaflets 26a, 26b mounted therein. The valve body 22 may be fabricated using a graphite core coated with pyrolytic carbon as described in U.S. Pat. No. 4,276,658. Other biocompatible materials such as titanium may also be suitable.

To facilitate attachment of the heart valve 20 to the heart tissue, a sewing cuff assembly 32 incorporating an embodiment of the present invention is mounted to the valve body 22. The sewing cuff assembly 32 includes a soft cuff fabric 34 that may be sutured to the surrounding heart tissue to secure the heart valve 20 in the desired position in place of the removed natural valve structure. In order to facilitate adjustment of the valve body 22 after implantation, the sewing cuff assembly 32 according to the invention is rotatable relative to valve body 22.

In accordance with the invention, the sewing cuff assembly 32 includes a resiliently deformed spring, which cooperates with a circumferential surface 36 of the valve body 22 to control the torque required to rotate the sewing cuff 32 relative to the valve body 22. Referring to FIG. 2, the spring exerts a controlled inwardly directed radial force on the circumferential surface 36 of the valve body 22. Alternatively, or in addition, the spring may be configured to exert an axially directed force against the annular shoulders 38a, 38b. As a result of this controlled force, and the friction generated thereby, the valve body 22 resists rotation relative to the sewing cuff assembly 32, and will prevent rotation until an appropriate level of torque is applied. Once the restraining torque is exceeded, the body 22 and cuff assembly 32 may be rotated relative to one another. Thus, during implantation surgery, the cardiovascular surgeon can rotate the valve body 22 to the most advantageous position by applying a torque in excess of the restraining torque. At applied torque levels less than the restraining torque, the body 22 and cuff assembly 32 resist relative rotation. As a result, the body 22 and cuff assembly 32 will not rotate during the normal operation of the valve 20 after implantation.

According to an important aspect of the invention, the design permits the restraining torque to be controlled within a predictable and desirable range. In the embodiment shown in FIG. 2, annular shoulders 38a, 38b are provided along each side of the circumferential surface 36 such that the surface 36 forms an annular seat in which the sewing cuff assembly 32 may be mounted. While such an annular seat is not required for operation of the invention, such a seat enhances axial cuff retention. Accordingly, the following description of various embodiments of the invention will refer to the sewing cuff 32 being mounted in an annular seat 36, rather than merely a circumferential surface. (For the remainder of the description, the annular seat will be referred to by reference numeral 36.) It will be appreciated, however, that annular shoulders 38a, 38b are not required for the invention to function, and that the cuff 32 might likewise be mounted in a circumferential surface that is not flanked by annular shoulders 38a, 38b.

The currently preferred embodiment of the invention is shown in cross-section in FIG. 2. In this embodiment, the spring comprises a helical spring 42. During manufacture, a wire is wound to create the revolutions of the helical spring 42. According to an important aspect of the invention, the free inside diameter of the wound helical spring 42 is smaller than the diameter of the annular seat 36. During assembly, the helical spring 42 is expanded and placed within the annular seat 36 of the valve body 22, and the spring 42 compresses and captures the fabric 34 between itself and the valve body 22, creating a controlled inwardly-directed radial force. While the spring 42 resiliently deforms about the valve body 22, it will be appreciated that the spring may deform both elastically and plastically. It will be appreciated, however, that it is the elastic deformation which primarily results in the torque-resisting radial force.

The free diameter and number of revolutions of the helical spring 42 about the valve body 22 is dependent upon the thickness of the wire itself and the spring constant, thereof, the width of the annular seat 36, and the desired rotation-resisting torque. Preferably, the adjacent revolutions of the helical spring 42 are relatively close to one another when wound about the valve body 22 and lie flat within the annular seat 36 once assembled. In the embodiment illustrated, the helical spring 42 makes approximately 2¾ revolutions around the valve body 22. It will be appreciated, however, that the wire might be sized different and/or wound a different number of revolutions depending upon the specific geometry of the valve body and the characteristics desired.

While the spring might have an alternate cross section, such as rectangular or round (as will be described with reference to alternate embodiments), the wire of the helical spring 42 of the preferred embodiment of the invention has a substantially square cross-section. As a result, the adjacent coils of the helical spring 42 may be disposed such that they present a substantially smooth and continuous surface toward the fabric 34 of the cuff assembly 32. In this way, the inner surface of the helical spring 42 applies an inwardly-directed radial force on the fabric 34 and in turn on the valve body 22.

The spring may be formed from a biocompatible material, which has long term corrosion resistance, and appropriate strength, rigidity, radiopacity, creep and fatigue characteristics. The currently preferred material is Elgiloy®, a cobalt-chrome-nickel alloy [ASTM F 1058]). Other appropriate spring materials may include MP35N, nickel-titanium alloys, titanium and stainless steel. Other biocompatible materials, including polymers, are within the comtemplation of the invention.

In order to enhance cuff retention and resistance to external forces, a restraining ring element or assembly 44 may be provided. In the embodiment shown, the restraining ring element comprises two individual restraining rings 46, 48. As may be seen in FIG. 2, the restraining ring element 44 is disposed circumferentially about the spring 42 to constrain radial expansion of the spring 42. In this way, the restraining ring element 44 ensures that the coils of the spring 42 remain in the flat position shown in FIG. 2, preventing the coils from being pulled radially away from the annular seat and/or riding up over the shoulders. Thus, the restraining ring element 44 helps to retain the spring in the annular seat and minimizes the creation of a "gap" from occurring between the cuff assembly 32 and the valve body 22, as might happen, for example, when a lateral force is applied.

To assist in properly locating the restraining ring element 44 along the outer circumference of the spring 42, the restraining ring element 44 is provided with flanges 46a, 48a which extend radially inward. The flanges 46a, 48a engage the lateral edges of the spring 42 to limit the lateral movement of the restraining ring element 44 relative to the spring 42 and the valve body 22.

In order to facilitate simple and reliable assembly of the heart valve assembly 20, the restraining ring element 44 of the embodiment shown in FIG. 2 is preferably split and comprises two individual restraining rings 46, 48 that may be separately assembled onto the valve body 22. Preferably, the restraining rings 46, 48 are identical, each having a flange 46a, 48a extending radially inwardly.

It will be appreciated, however, that the restraining ring element may comprise a single restraining ring (as will be described with regard to later embodiments), two restraining rings (as described with regard to the embodiment shown in FIG. 2), or, alternately, even three or more individual restraining rings. Moreover, the restraining ring element 44 need not necessarily include two flanges. The restraining ring element 44 might comprise only one, or no laterally extending flanges.

Inasmuch as the restraining ring element 44 is disposed adjacent the spring 42, the restraining ring element 44 should be formed from a material which will not result in galvanic interaction when the valve assembly is implanted in the body. In the preferred embodiment of the invention, the restraining rings 46, 48 are manufactured from MP35N (ASTM F 562). However, alternate materials such as titanium, Elgiloy®, and polymers such as Delrin® may be equally suitable, so long as they provide adequate strength, structural integrity, resistance to corrosion and are biocompatible. Other biocompatible materials and polymers are within the contemplation of the invention.

According to an important feature of the invention, the spring 42 compensates for component tolerance extremes. Torque control is influenced by the dimensions of the spring 42 and the fabric 34, and the external dimensions of the valve body 22. The resilience of the spring 42 compensates for some variances in the tolerances of these components such that the final resistance to torque demonstrated by valves 20 constructed in accordance with the invention is highly consistent. For example, in prototype evaluation, a large number of valves constructed according to the design shown in FIG. 2 had an average torque after sterilization of 5.44 in-oz with a standard deviation of 0.85 in-oz. based on an approximately normal distribution.

According to another important feature of the invention, the heart valve 20 may be easily and accurately assembled. FIG. 3 illustrates a preferred assembly fixture for use in assembling the rotatable cuff 32 according to the present invention to the heart valve 20. It will be appreciated, however, that any appropriate assembly device may be utilized.

To support the valve body 22 during assembly, a base assembly 50 having two upstanding probes 50a, 50b is provided. The valve body 22, in which the leaflets 26a, 26b have been preassembled, is slid down onto the base assembly 50 with the pivot guards 22a, 22b facing downward. It will be appreciated that the probes 50a, 50b of the base assembly 50 extend upward through the valve body 22 and past the open leaflets 26a, 26b. A retainer slide 52 having outwardly extending flanges 52a, 52b is then inserted into the base assembly 50 through channels 50c, 50d. The retainer slide 52 is used as a receptacle for mandrel screw 55.

To further assist in assembling the valve 20, a conically-shaped mandrel 54 is provided. Prior to assembling the mandrel 54 to the base assembly 50, the cuff fabric 34, one end of which has been folded over on itself and sewn to form a flange 34a, is slid down over the mandrel 54 until about 0.5 inch of the cuff fabric 34 extends past the wide end of the mandrel 54. That portion of the cuff fabric 34 extending beyond the mandrel 54 is then tucked up inside a large bore 54a which opens to the bottom of the mandrel 54. In assembling aortic valves, as shown in FIGS. 1 and 2, the flanged end 34a of the cuff fabric 34 is tucked into the bore 54a, while with mitral valves, the opposite end 34b of the cuff fabric 34 is tucked into the bore 54a.

The mandrel 54, to which the cuff fabric 34 has been assembled, is then slid down over the probes 50a, 50b of the base assembly 50, to which the valve body 22 and retainer slide 52 had been previously assembled. The mandrel 54 is securely seated on the base assembly 50 such that the cuff fabric 34 is pinched between the mandrel 54 and the valve body 22.

In order to secure this assembly together, a mandrel screw 55 is provided. The mandrel screw 55 comprises a conically shaped head 55a from which a threaded shaft 55b extends. The shaft 55b is inserted through a relatively small bore 54b extending through the mandrel 54, and into the retainer slide 52. To couple the base assembly 50, mandrel 54, and mandrel screw 55 together, the retainer slide 52 is provided with a threaded hole 52c which receives the end of the mandrel screw threaded shaft 55b. The mandrel screw 55 is then finger tightened into the hole 52c to provide a assembly. The cuff fabric 34 is then slid down the mandrel 54 and over the valve body 22, the cuff fabric 34 turning inside out as it is slid down.

In order to assist in assembling the restraining rings 46, 48 and spring 42 onto the valve body 22 about which the cuff fabric 34 has been assembled, a driver 58 may be provided which may be slidably positioned over the mandrel 54 and mandrel screw conical head 55a. The driver 58 shown has a generally cylindrical shape with flexible fingers 58a which separate as the driver 58 slides down the mandrel 54. To maintain the fingers 58a of the driver 58 in close contact with the mandrel 54 during use, a rubber o-ring 58b is disposed about the fingers 58a. The driver 58 may be of any appropriate flexible, resilient material. Delrins® has been found to be a suitable material. The driver 58 may be used to push components down the mandrel and into position on the valve body 22, the fingers 58a spreading, but maintaining contact with both the mandrel 54 and the component as they slide along the surface of the mandrel 54.

In assembling the cuff fabric 34 to the heart valve 20, a first restraining ring 46 is positioned on the mandrel 54 with the flange 46a disposed downward. The driver 58 is then used to push the first restraining ring 46 down the mandrel 54 into the proper position on the valve body 22 over a layer of fabric 34 in the annular valve seat 36. The driver 58 may then be used to push the spring 42 into position, the spring 42 expanding as it slides down the mandrel 54 so that it may be seated in the annular seat 36. The driver 58 may then be used to push the second restraining ring 48 having the flange 48a disposed upward into the proper position. The assembler may then use his fingers or a soft tool to adjust the positions of the restraining rings 46, 48 to completely cover the spring 42.

Once the spring 42 and restraining rings 46, 48 are in place, the mandrel screw may be loosened and removed, and the mandrel 54 lifted from the base assembly 50. The retainer slide 52 is then slid sideways from the probes 50a, 50b of the base assembly 50 so that the valve assembly may be removed. The cuff assembly 32 may then be sewn to form a toroidal shape.

The valve 20 may then be sterilized by any accepted sterilization method; however, steam sterilization is currently used. In addition to compensating for some variances in component tolerance extremes, the resilience of the spring additionally helps to minimize any change in torque resulting from relaxation of fibers in the sewing cuff fabric during the steam sterilization process.

A first alternate embodiment of the invention is shown in FIG. 4. In this embodiment, the spring includes a helical spring 66 that has a substantially round cross section. As with the preferred embodiment of the invention, the helical spring 66 is oriented substantially coaxially with the annular valve seat 36. The helical spring 66 may be formed from a wire in a manner similar to that described with regard to the first embodiment of the invention, and may be similarly assembled. The ends of the helical spring 66 may be end-ground.

The embodiment shown in FIG. 4 includes no restraining rings. It will be appreciated, however, that a two part ring element 70, 72 or a single ring element 74 may be provided, as in the embodiments illustrated in FIGS. 5 and 6, respectively. As with the first embodiment of the invention (FIG. 2), the restraining rings 70, 72, 74 preferably include radially extending flanges 70a and 72a, 74a and 74b, respectively. The restraining rings in these embodiments perform in substantially the same manner as described above with regard to FIG. 2. It will be appreciated, however, that the one piece ring element 74 shown in FIG. 6 may be assembled only after the spring 66 is properly positioned about the valve body 22.

In the embodiment shown in FIG. 7, a thin foil strip 76 of biocompatible material, such as Elgiloy®, Delrin®, or similar material is shown disposed between the helical spring and the fabric 34, within the annular seat 36. The foil strip 76 may be a continuous ring or a strip which is laid along the fabric 34 about the circumference of the annular seat 36. In this way, the coils of the spring 66 bear against the foil strip 76 such that the foil strip 76 distributes and transmits a substantially uniform inwardly-directed radial force to the seat 36. Additionally, the foil strip 76 helps to prevent the ends of adjacent coils of the spring 66 from pulling away from the annular valve seat 36, and, therefore, minimizes the opportunity for the formation of a gap between the cuff assembly 32 and the valve body 22.

Another embodiment of the invention which utilizes a different configuration of spring is shown in FIGS. 8 and 9. In this embodiment, the helical spring 80 may have its ends joined together to form a toroidal shape, with the helical diameter of the spring 80 being small compared to the toroidal diameter such that the circumferential length of the torus formed by the spring is approximately the circumference of the annular seat 36. Springs of this general type, but used for sealing applications, are shown, for example, in U.S. Pat. Nos. 4,655,462, 4,826,144, and 4,915,366 to Balsells. As used in the present invention, the elastic deformation of the spring 80 is provided by deforming and confining it between a restraining ring element 82 and the valve body 22. As may be seen in FIG. 8, the inside diameter of the ring element 82 forms an annulus 86 with the annular seat 36. The spring 80 is disposed within the annulus 86. That is, the spring 80 is laid into the annular seat 36 about the circumferential surface of the valve body 22, rather than the individual coils of the spring being wound about the valve body 22 (as in the embodiments shown in FIGS. 2 and 4–7). The relative sizes of the ring element 82 and the annular valve seat 36 are such that the spring 80 disposed within this annulus 86 deforms between these two restraining surfaces 84, 36, canting, as shown in FIG. 9. It will thus be appreciated that the ends of the spring 80 need not be joined, so long as the spring is deformed in the annulus 86 formed between the annular seat 36 and the inside diameter of the ring element 82.

The resiliently deformed spring 80 exerts an outwardly directed radial force, which is opposed by the restraining ring element 82, and a controlled inwardly directed radial force to the annular orifice seat 36. It is this inwardly directed radial force that results in a rotation-resisting torque sufficient to resist rotation during normal operation of the valve 20 after implantation, but low enough to permit assisted rotation during the implantation operation.

In order to present a substantially even force applying surface to the fabric 34 disposed within the annular orifice seat 36 and in order to enhance cuff retention, an inner ring 88 may be provided. The inner ring 88 helps facilitate the assembly of the valve by providing an interface between the spring 80 and the cuff 34. Moreover, the ring 88 assists in cuff retention by minimizing the opportunity for formation of a gap between the cuff assembly 32 and the annular seat 36. The inner ring 88 may be a continuous or split ring. Preferably, however, the inner ring 88 includes centering flanges 88a, 88b that extend radially outward to create a channel that holds the spring 80 in position. It will be appreciated that centering flanges might alternately be provided that extend inwardly from the ring element 82. For ease of assembly, however, it is preferable that the flanges 88a, 88b extend outwardly from the inner ring 88. The inner ring 88 may be of any appropriate material which meets the criteria set forth above with regard to the restraining ring element 46, 48. It will be appreciated, however, that, in order to facilitate assembly, the ring 88 must be formed of a resilient material if the ring 88 is formed as a continuous ring.

It will be appreciated that, rather than canting the spring 80 between the restraining ring element 82 and the orifice seat 36 or inner ring 88, an uncanted spring having its ends joined might alternately be utilized. The innermost diameter of the toroidal shape of the uncanted spring, however, must be comparatively smaller than the diameter of the annular seat 36 such that the spring provides an inwardly directed force, similar to that in the FIG. 2 embodiment. Although not required for operation of the valve, the ring element 82 or the inner ring 88 may likewise be provided in order to enhance cuff retention.

Yet another embodiment of the invention which comprises a confined spring is shown in FIGS. 10 and 11. In this embodiment, however, a spring 90 with an undulating "wave" configuration is utilized. The wave spring 90 may be an undulating strip of a resilient material similar to that utilized for the springs of the other embodiments. The wave spring 90 may be of a strip form that may be laid into the annular valve seat 36, or of a continuous, generally annular shape. The wave spring 90 is disposed within the annulus 86 formed between the ring element 82 and the annular valve seat 36 as in the embodiment shown in FIGS. 8 and 9. In this embodiment, however, no inner ring is shown. It will be appreciated that the wave spring 90 presents smooth surfaces to the fabric 34 at intervals dictated by the period of the undulations.

An alternative spring configuration is shown in FIGS. 12 and 13. The spring 92 utilized in this embodiment is shown essentially as an eight-pointed "star," although, any number of bends may be provided so long as the desired resiliency is obtained. The spring 92 has a continuous generally annular shape. When assembled within the heart valve, the spring 92 may be expanded to fit about the circumferential surface of the valve body in a manner similar to that described above with regard to the embodiments shown in FIGS. 2 and 4–7. In this way, the spring 92 may be resiliently deformed as a result of the relationship between the spring 92 and the circumferential surface. Alternately, the spring 92 may resiliently deform in much the same manner as described above with regard to the undulating spring (FIGS. 10 and 11). That is, the spring 92 may be resiliently deformed within an annulus formed between the circumferential surface and the inner surface of a restraining ring element.

The "star" spring may also be utilized with a valve body 22 having a "tented" annular valve seat 96. The spring 94 of this embodiment has a design similar to that shown in FIGS. 12 and 13. In this embodiment, however, the inner bends (designated as 92a in the spring shown in FIG. 12) of the octagonal spring 94 are provided with apertures 94a, as shown in FIG. 15. When the spring 94 is assembled into the annular seat 96, the tent 96a of the valve seat 96 extends into the apertures 94a to maintain the spring 94 in axial alignment and minimize the outside diameter of the spring 94.

In summary, heart valve prostheses constructed in accordance with the invention provide a predictable level of rotation resisting torque over a desired range. The present invention permits the resilience of the spring to compensate for relaxation of other components of the valve, such as the cuff fabric, which may occur during the sterilization processes and thereafter, and to minimize the change in torque as a result of that relaxation.

Further in this regard, the resilience of the spring compensates for some variations in the other components of the valve, such as minor manufacturing variations in the orifice dimensions and differences in the thickness and other minor variations in the fabric. This reduces dependence on individual assembler skill and valve-to-valve consistency.

Moreover, because the spring can be manufactured with well known technology to a predictable level of force, a target manufacturing range for desired torque levels may be established and maintained within design limits in the final product. As a result, the invention yields heart valve prostheses which employ well known technology to result in a valve which may be easily adjusted by the surgeon during implantation, yet resist spontaneous rotation after implantation.

Another advantage of the rotatable valve design is that it may employ common or known fabric and valve bodies or orifices, as in the case of the referenced commercial valve embodying the valve disclosed in U.S. Pat. No. 4,276,658, such that the size, configuration and appearance of the rotatable valve are very similar to the current design non-rotatable valve. This may minimize regulatory approval issues and permit established implantation procedures to be continued.

Further in this regard, the rotatable cuff design is also extremely compact and, in the case of the referenced commercial valve embodying the valve disclosed in U.S. Pat. No. 4,276,658, it does not significantly increase the diameter of the sewing cuff over the heretofore standard, non-rotatable cuff design. As a result, the internal diameter of the orifice may be maintained at a maximum to ensure maximum blood flow once implanted.

Moreover, the rotatable heart valve is of a relatively simple design and may be readily and consistently assembled using a conically shaped assembly fixture. As a result, heart valves having the desired consistent torque-resisting characteristics may be economically manufactured in the volumes required.

Further, the valve may be implanted using the most advanced surgical techniques. More specifically, the metal components of the rotatable cuff design are more reliable against cutting edge needles than is the case with existing cuffs secured to the valve with conventional sutures. After implantation, the orientation of the rotatable valve may according to the invention be verified by X-ray inasmuch as the ring elements and springs will increase the degree of radiopacity.

It is to be understood the claims appended hereto are to be accorded a range of equivalence commensurate in scope with the advance over the prior art.

We claim as our invention:

1. A heart valve prosthesis comprising a generally annular orifice structure having an outer circumference and two circumferential shoulders extending in a radially outward direction from the outer circumference, the heart valve substantially blocking fluid flow through the orifice structure in one direction and permitting fluid flow through the orifice structure in the direction opposite to the first direction, and further including a sewing cuff assembly mounted to the orifice structure, the sewing cuff assembly comprising a resiliently deformed spring extending around the outer circumference of the orifice structure positioned between the two circumferential shoulders and having a shape which is resiliently deformable in a radial direction, the spring for actively and independently exerting a controlled force directed substantially radially inward on a surface of the outer circumference of the orifice structure due to a substantially radially outward deformation in the shape of the spring, the surface causing the deformation of the spring to thereby provide the controlled force which is selected to result in a rotation-resisting torque sufficient to resist rotation during normal operation of the valve after implantation but low enough to permit assisted rotation and wherein the radially inward force causes the resiliently deformed spring to be captured between the two circumferential shoulders which thereby substantially secure the spring from movement in an axial direction.

2. The heart valve prosthesis of claim 1 wherein the resiliently deformed spring exerts a controlled inwardly directed radial force on the circumferential surface of the orifice structure.

3. The heart valve prothesis of claim 1 wherein the resiliently deformed spring exerts a controlled axially directed force.

4. The heart valve prosthesis of claim 1 wherein the sewing cuff is mounted on the orifice by the force exerted by the resiliently deformed spring.

5. The heart valve prosthesis of claim 2 wherein the spring exerts the radial force through at least one layer of the fabric which is rotatable relative to the orifice structure.

6. The heart valve prosthesis of claim 2 wherein the spring is a helical spring oriented substantially coaxially with the circumferential surface of the orifice, the spring comprising at least one revolution, the free inside diameter of the helical spring being smaller than that assumed by the spring when in place over the circumferential surface, resulting in the application of a controlled inwardly directed radial force to the circumferential surface.

7. The heart valve prosthesis of claim 6 wherein the cross section of the helical spring is substantially rectangular.

8. The heart valve prosthesis of claim 7 wherein the cross section of the helical spring is substantially square.

9. The heart valve prosthesis of claim 6 wherein the cross section of the helical spring is substantially round.

10. The heart valve prosthesis of claim 2 wherein the spring is a substantially annular undulating spring oriented substantially coaxially with the circumferential surface, the spring having transitional sections defining an inside diameter and transitional sections defining an outside diameter, the free inside diameter of the undulating spring being smaller than that assumed by the spring when in place over the circumferential surface, resulting in the application of a controlled inwardly directed radial force to the circumferential surface.

11. The heart valve prosthesis of claim 10 wherein the transitional sections are relatively pointed.

12. The heart valve prosthesis of claim 2 wherein the sewing cuff assembly further comprises a ring element to circumferentially constrain the radial expansion of the spring about the entire circumference of the spring.

13. The heart valve prosthesis of claim 12 wherein the ring element has at least one flange extending radially inwardly to engage a lateral edge of the spring element to limit the lateral movement of the ring element relative to spring.

14. The heart valve prosthesis of claim 13 wherein the ring element has two radially extending flanges spaced axially to engage the opposed lateral edges of the spring element to maintain the spring element between the flanges.

15. The heart valve prosthesis of claim 12 wherein the sewing cuff assembly comprises two ring elements, each having a radially extending flange, the rings being oriented and the flanges being spaced to engage the opposed lateral edges of the spring element to maintain the spring element between the flanges.

16. The heart valve prosthesis of claim 2 wherein the orifice structure further comprises opposed retaining shoulders on each side of the circumferential surface, the inside diameter of the spring being sized relative to the outside diameter of the shoulders such that, once the spring is assembled between the shoulders, the spring must undergo forced radial expansion to be moved out of alignment in the axial direction with the circumferential surface.

17. The heart valve prosthesis of claim 11 wherein the transitional sections disposed defining the inner diameter of the spring comprise apertures, and the circumferential surface comprises an annular peak, the apertures of the spring being disposed along the peak once the spring is assembled such that the spring ring must undergo forced radial expansion to be moved out of alignment in the axial direction with the circumferential surface.

18. The heart valve prosthesis of claim 2 further comprising a ring element co-axial with and having an inside diameter larger than the circumferential surface to form an annulus therebetween wherein the spring is resiliently deformed within the annulus, the deformation resulting in the application of a controlled inwardly directed radial force to the circumferential surface.

19. The heart valve prosthesis of claim 18 wherein the spring is an undulating spring member resiliently constrained in the annulus created between the ring element and the circumferential surface.

20. The heart valve prosthesis of claim 18 wherein the spring is a helical spring having a diameter substantially smaller than the diameter of the annular surface but greater than the radial dimension of the annulus between the circumferential surface and the ring element and having a length about equal to the circumference of the circumferential surface, the coils of the spring being resiliently deflected into the annular space.

21. The heart valve prosthesis of claim 2 further comprising a ring element disposed between the spring and the surface of the orifice structure.

* * * * *